United States Patent
Kessel et al.

(10) Patent No.: US 6,415,646 B1
(45) Date of Patent: Jul. 9, 2002

(54) METHOD FOR MEASURING GAS CONCENTRATIONS

(75) Inventors: Robert Kessel, Bad Oldesloe; Marko H. Wittich, Lübeck, both of (DE)

(73) Assignee: Dräger Sicherheitstechnik GmbH, Lübeck (DE)

(*) Notice: Subject to any disclaimer, the term of this patent is extended or adjusted under 35 U.S.C. 154(b) by 0 days.

(21) Appl. No.: 09/456,993

(22) Filed: Dec. 7, 1999

(30) Foreign Application Priority Data

Dec. 16, 1998 (DE) .......................... 198 58 022

(51) Int. Cl.$^7$ .................. G03B 17/24; G03B 29/00; G01M 3/04; G01N 1/22
(52) U.S. Cl. .................. 73/23.2; 73/31.01; 340/632
(58) Field of Search .................. 73/23.2, 31.02, 73/40, 31.01; 340/632, 601

(56) References Cited

U.S. PATENT DOCUMENTS

| | | | | |
|---|---|---|---|---|
| 3,521,493 A | * | 7/1970 | Guizouarn et al. | 73/421.5 |
| 5,025,653 A | * | 6/1991 | Schuldt | 73/1 G |
| 5,184,502 A | * | 2/1993 | Adams et al. | 73/31.01 |
| 5,604,299 A | * | 2/1997 | Cobb | 73/31.02 |
| 5,913,078 A | * | 6/1999 | Kimura et al. | 396/50 |
| 5,983,705 A | * | 11/1999 | Kitaoka et al. | 73/31.01 |
| 6,094,968 A | * | 8/2000 | Scheufler et al. | 73/23.2 |
| 6,104,301 A | * | 8/2000 | Golden | 340/628 |
| 6,198,400 B1 | * | 3/2001 | Church et al. | 340/632 |
| 6,212,937 B1 | * | 4/2001 | Hubert et al. | 73/23.2 |

FOREIGN PATENT DOCUMENTS

| | | |
|---|---|---|
| DE | 2655271 | 6/1978 |
| DE | 4423623 | 1/1996 |
| DE | 196 14 231 | 10/1997 |
| EP | 0624797 | 11/1994 |
| EP | 0837328 | 4/1998 |
| GB | 2323672 | 9/1998 |

OTHER PUBLICATIONS

"Miniaturized Carbon Monoxide Sonde for Atmospheric Measurements" by J. Bognar et al, Analytical Chemistry, vol. 70, No. 18, Sep. 1998, pp. 3874 to 3879.

* cited by examiner

Primary Examiner—Hezron Williams
Assistant Examiner—David J. Wiggins
(74) Attorney, Agent, or Firm—Walter Ottesen

(57) ABSTRACT

The invention is directed to a method for measuring gas concentrations with a measuring head which is provided with a satellite-supported global positioning device. With the method, gas concentrations at various locations can be determined. The position of the measuring head is determined at predetermined time intervals and first position data of a previously measured first position is compared to second position data of a current position. When a predetermined limit value between the first position data and the second position data is exceeded; a measured value of gas concentration corresponding to the current position together with the second position data are stored in a data memory of the measuring head.

3 Claims, 1 Drawing Sheet

METHOD FOR MEASURING GAS CONCENTRATIONS

FIELD OF THE INVENTION

The invention relates to a method for measuring gas concentrations with a measuring probe which is supported with a global positioning system (GPS).

BACKGROUND OF THE INVENTION

German patent publication 196 14 231 discloses a measuring device with a satellite-supported global positioning system in the form of an emergency calling device which is carried on the body of a patient and continuously measures certain vital parameters of the patient. When an emergency arises, the vital parameters and the current position data are transmitted to a central emergency call station. The known measuring device is intended to provide a fast and directed emergency response.

Devices for measuring gas concentrations at different locations are known. These devices are comprised of individual measuring heads which are arranged in a plurality of spaces. The measured values are transmitted to a central evaluation unit. Such a device is disclosed, for example, in German patent publication 26 55 271.

The disadvantage of this known measuring system is that the gas concentration measurements can be performed only at very precisely predetermined measuring locations.

SUMMARY OF THE INVENTION

It is an object of the invention to provide a method for measuring gas concentrations which permits gas concentrations to be detected at different locations in a simple manner.

A first embodiment of the method of the invention is for measuring gas concentrations with a measuring head having a data memory and communicating with a satellite-supported global positioning system. The method includes the steps of: determining position data of a position of the measuring head at preset time intervals and measuring gas concentration values at the position of the measuring head; comparing first position data of a previous first position of the measuring head with second position data corresponding to a current position of the measuring head and determining whether a predetermined limit value is exceeded; and, if the predetermined limit value is exceeded, storing the second position data together with a measured value of gas concentration corresponding to the current position in the data memory of the measuring head.

The advantage of the method of the invention is essentially that the measuring head, provided with a satellite-supported global positioning system, continuously determines the current position, compares this current position with a previously measured position, and stores the current position data together with a measured value of gas concentration in a memory of the measuring head when a significant positional change occurs. In this way, it is possible to establish a toxic substance register of the environment to be tested.

A second embodiment of the method of the invention includes the steps of: determining the position of the measuring head and measured values of gas concentration corresponding to the position at preset time intervals and storing the position and the measured values of gas concentration in the data memory of the measuring head; detecting current measured values of gas concentration within the time intervals; comparing the current measured value of gas concentration with a measured value of gas concentration last stored in the data memory to obtain a difference concentration measured value; and, if the difference concentration measured value exceeds a predetermined difference concentration threshold value, storing the current measured value of gas concentration in the data memory of the measuring head.

This advantageous second method of the invention is applicable in cases wherein a change of the gas concentration over time is to be measured.

For this purpose, the position of the measuring head and the measured value of gas concentration, which corresponds to that position, are determined at predetermined time intervals and the data are stored in the data memory of the measuring head. Further gas concentration values are detected within the time intervals and, in each case, compared to the gas concentration value stored last. A difference concentration measuring value is formed from the current measured gas concentration value and the measured gas concentration value stored last. The current measured gas concentration value is stored in the data memory only when the difference concentration measured value exceeds a predetermined threshold value. In this manner, significant gas concentration changes within the time intervals can be detected and documented.

Advantageously, the measured gas concentration values stored in the measuring head and the position data are transmitted to an evaluation unit in which the toxic substance register is generated. The transmission can take place, as is-known in the art, via a PC interface or via wireless transmission. When several measuring heads are provided, which transmit position data and measured gas concentration values to the evaluation unit, the position data can be used to determine the spacing of the measuring heads relative to one another or to calculate an average gas concentration along a measuring path between two measuring heads.

When several measuring heads are present, it is advantageous. to transmit to the evaluation unit the stored position data and the measured gas concentration values together with identifiers assigned to the measuring heads, respectively.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
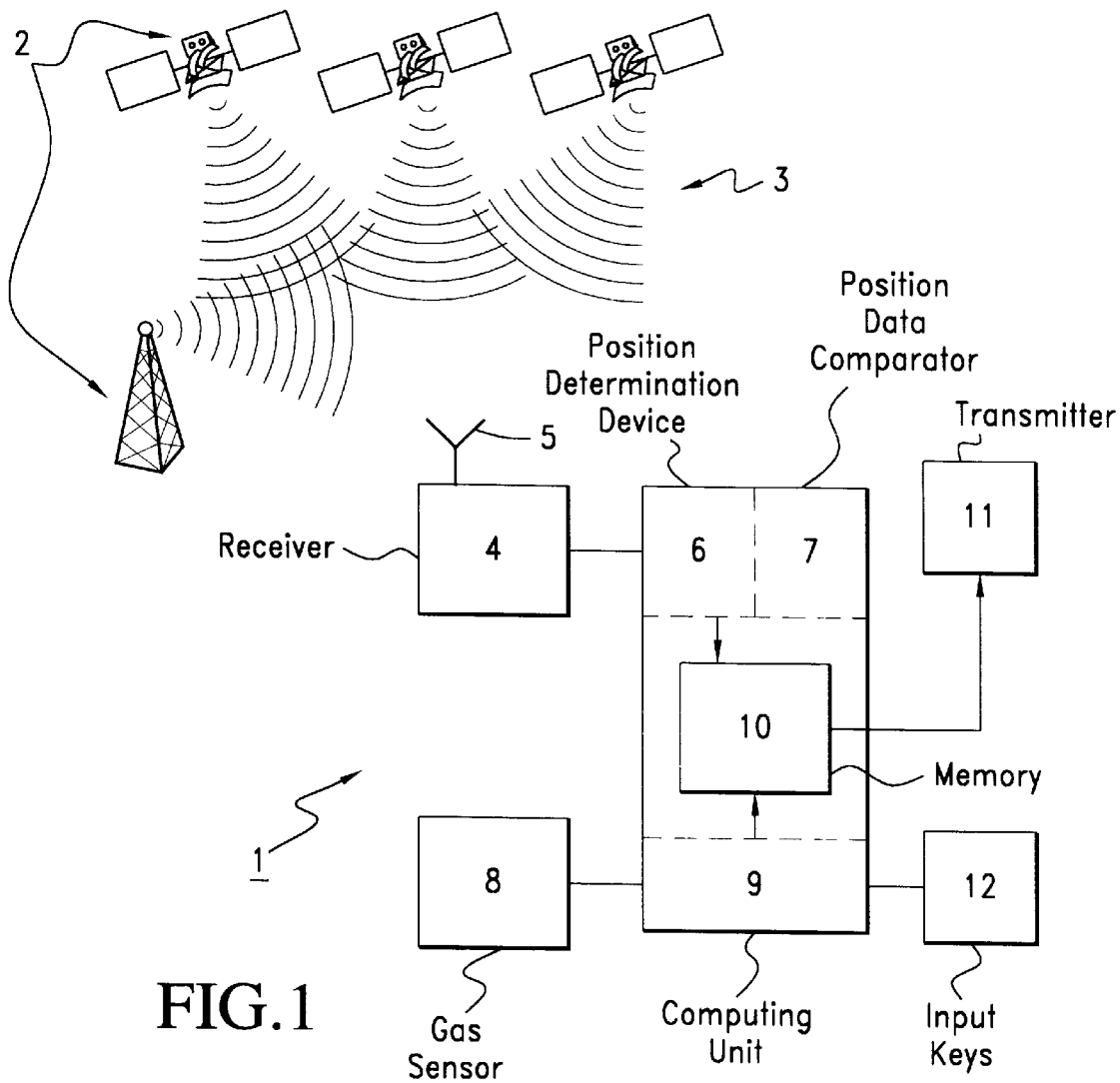
FIG. 1 is a schematic of a measuring head with a satellite-supported global positioning system in accordance with an embodiment of the method of the invention; and, FIG. 2 is a schematic view of an evaluation unit utilized with the method of the invention.

In FIG. 1, a measuring head 1 is shown which is adapted to receive the GPS signals 3 sent by the position transmitters 2. The measuring head 1 has a receiver 4 with a receiving antenna 5, a position determination device 6 having a position data comparator 7, a gas sensor 8 connected to a computing unit 9 with a memory 10, a transmitter 1, and input keys 12 via which an identifier specific to the measuring head 1 can be inputted to the computing unit 9.

Figure 2:
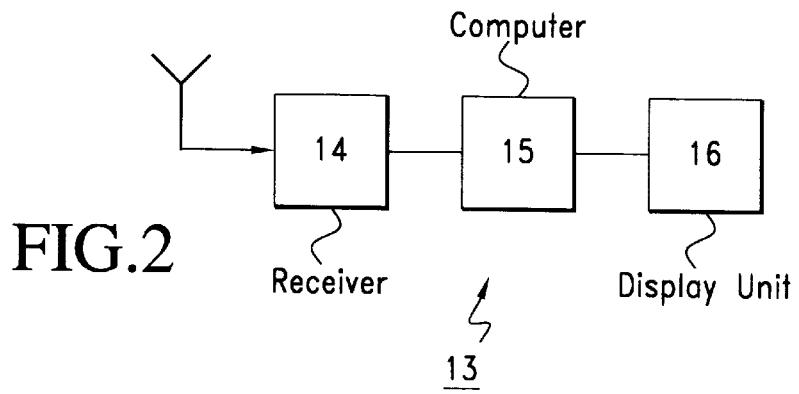

The evaluation unit 13 shown in FIG. 2 receives via a receiver 14 the position data and measured gas concentration values transmitted by one or more measuring heads 1. A computer 15 is arranged downstream of the receiver 14. The received measured values are displayed via a display unit 16 on a monitor (not shown in FIG. 2).

The method of the invention operates as described below.

The receiver 4 continuously receives GPS signals 3 from which the position determination device 6 calculates current position data. Simultaneously, the toxic gas content in the vicinity of the measuring head 1 is continuously measured by the gas sensor 8. Measured gas concentration values are calculated by the computer unit 9 from the signals supplied by the gas sensor 8.

Before starting the measurements, either an identifier specific to the measuring head 1 or a user-specific identifier is inputted to the computing unit 9 via the input keys 12 and stored in the memory 10. The position data comparator 7, which receives new position data from the position determination device 6 at predetermined time intervals, compares the current position data with position data of a previous position. When a position change occurs, which is detected when a limit value is exceeded during the position data comparison, the current position data together with the corresponding measured gas concentration value are stored in the memory 10.

If the position of the measuring head 1 is not changed and the measured gas concentration values are to be determined at a fixed location, the detection of the measured gas concentration values is carried out at greater time intervals, and/or is triggered by a threshold value of the gas concentration. Thereafter, the measured gas concentration values and the unchanged position data are recorded in the memory 10. Accordingly, measured gas concentration values can be determined at different locations or the gas concentration can be measured as a function of time at a fixed location all without the user having to make any kind of adjustment at the measuring head. The course of the measurement can be precisely reproduced by correlating the measured gas concentration values with the position data and the time.

In the evaluation unit 13, the measured values received by the measuring head 1 are displayed to the user as a toxic substance register on a monitor of the display unit 16. Processing of the measuring values is performed by the computer 15. For example, the measuring head 1 can record measured values during a walk through a manufacturing facility and can transmit the data continuously to the evaluation unit 13. When a limit value of the toxic substance is exceeded, this can be immediately recognized with the evaluation unit 13.

It is understood that the foregoing description is that of the preferred embodiments of the invention and that various changes and modifications may be made thereto without departing from the spirit and scope of the invention as defined in the appended claims.

What is claimed is:

1. A method for measuring gas concentrations via at least one measuring head, said measuring head having a gas sensor, a data memory, a measuring head specific identifier and means for communicating with a satellite supported global positioning system, the method comprising the steps of:

determining position data of a position of the measuring head at preset time intervals via said satellite global positioning system and measuring gas concentration values with said gas sensor at the positions of the measuring head;

comparing first position data of a previous first position of the measuring head with second position data corresponding to a current position of the measuring head;

determining a difference position value between said first position data and said second position data;

comparing said difference position value with a predetermined limit position value;

if said predetermined position value is exceeded, storing said second position data together with said measured gas concentration value, corresponding to said second position, in said data memory of said measuring head; and, providing means for transmitting stored position data and corresponding gas concentration values together with said identifier to an evaluation unit.

2. The method of claim 1, comprising the further steps of:

detecting current measured values of gas concentration within said time intervals;

comparing said current measured values of gas concentration with a measured value of gas concentration last stored in said data memory;

determining a difference concentration value between the current measured value of gas concentration and said measured gas concentration value last stored in said data memory; and, if said difference concentration value exceeds a predetermined difference concentration threshold value, storing said current measured value of gas concentration in said data memory.

3. A method for measuring gas concentrations via at least one measuring head, said measuring head having a gas sensor, a data memory, a measuring head specific identifier and means for communicating with a satellite supported global positioning system, the method comprising the steps of:

determining the position of said measuring head via said satellite supported global positioning system and measuring values of gas concentration corresponding to said position at preset time intervals and storing the position and the measured values of gas concentration in said data memory of said measuring head;

detecting current measured values of gas concentration within said time intervals;

comparing said current measured values of gas concentration with a measured value of gas concentration last stored in said data memory;

determining a difference concentration value between the current measured value of gas concentration and said measured gas concentration value last stored in said data memory;

if said difference concentration value exceeds a predetermined difference concentration threshold value, storing said current measured value of gas concentration in said data memory in said measuring head; and, providing means for transmitting stored position data and corresponding gas concentration values together with said identifier to an evaluation unit.

* * * * *